United States Patent
Huebner

Patent Number: 5,824,108
Date of Patent: Oct. 20, 1998

[54] BIPOLAR ACETABULAR CUP

[75] Inventor: Randall J. Huebner, Aloha, Oreg.

[73] Assignee: Johnson & Johnson Professional, Inc., Raynham, Mass.

[21] Appl. No.: 824,778

[22] Filed: Mar. 26, 1997

[51] Int. Cl.⁶ ........................... A61F 2/32
[52] U.S. Cl. .................................... 623/22
[58] Field of Search .................. 623/18, 22, 23

[56] References Cited

U.S. PATENT DOCUMENTS

| | | |
|---|---|---|
| 3,818,512 | 6/1974 | Shersher . |
| 3,862,807 | 1/1975 | Doden et al. . |
| 3,889,299 | 6/1975 | Osborne et al. . |
| 4,004,300 | 1/1977 | English . |
| 4,241,463 | 12/1980 | Khovaylo . |
| 4,380,090 | 4/1983 | Ramos . |
| 4,619,658 | 10/1986 | Pappas et al. . |
| 4,624,674 | 11/1986 | Pappas et al. . |
| 4,676,798 | 6/1987 | Noiles ............................ 623/22 |
| 4,676,799 | 6/1987 | Legrand . |
| 4,714,477 | 12/1987 | Fichera et al. . |
| 4,718,911 | 1/1988 | Kenna . |
| 4,728,335 | 3/1988 | Jurgutis . |
| 4,770,658 | 9/1988 | Geremakis . |
| 4,770,661 | 9/1988 | Oh . |
| 4,798,610 | 1/1989 | Averill et al. . |
| 4,919,674 | 4/1990 | Schelhas . |
| 4,936,855 | 6/1990 | Sherman . |
| 5,009,665 | 4/1991 | Serbousek et al. . |
| 5,019,105 | 5/1991 | Wiley . |
| 5,049,158 | 9/1991 | Engelhardt et al. ............ 623/22 |
| 5,062,853 | 11/1991 | Forte . |
| 5,263,988 | 11/1993 | Huebner . |
| 5,314,491 | 5/1994 | Thongpreda et al. .......... 623/22 |
| 5,425,778 | 6/1995 | Zichner et al. ................. 623/22 |
| 5,425,779 | 6/1995 | Schlosser et al. .............. 623/23 |

FOREIGN PATENT DOCUMENTS

| | | |
|---|---|---|
| 4-58986 | 9/1992 | Japan . |
| 05344992 A | 12/1993 | Japan . |
| 4-181684 | 12/1993 | Japan . |

Primary Examiner—Michael J. Milano
Assistant Examiner—Tram Anh T. Nguyen
Attorney, Agent, or Firm—Kolisch, Hartwell, Dickinson, McCormack & Heuser

[57] ABSTRACT

An acetabular cup assembly for use with a femoral implant. The cup assembly includes an outer shell, a bearing liner configured to fit into a cavity in the shell, a generally annular retaining ring and a locking ring configured to hold the retaining ring in the shell adjacent the bearing liner. The locking ring is slidable between locked and free configurations, with at least part of the locking ring being formed as a closed loop to prevent radial contraction of the locking ring inner surface as the locking ring is slid between the free and locked configurations. At least one small circumferential rib is formed on the outer surface of the locking ring to engage a corresponding circumferential groove in the shell when the locking ring is installed therein in the locked configuration.

17 Claims, 3 Drawing Sheets

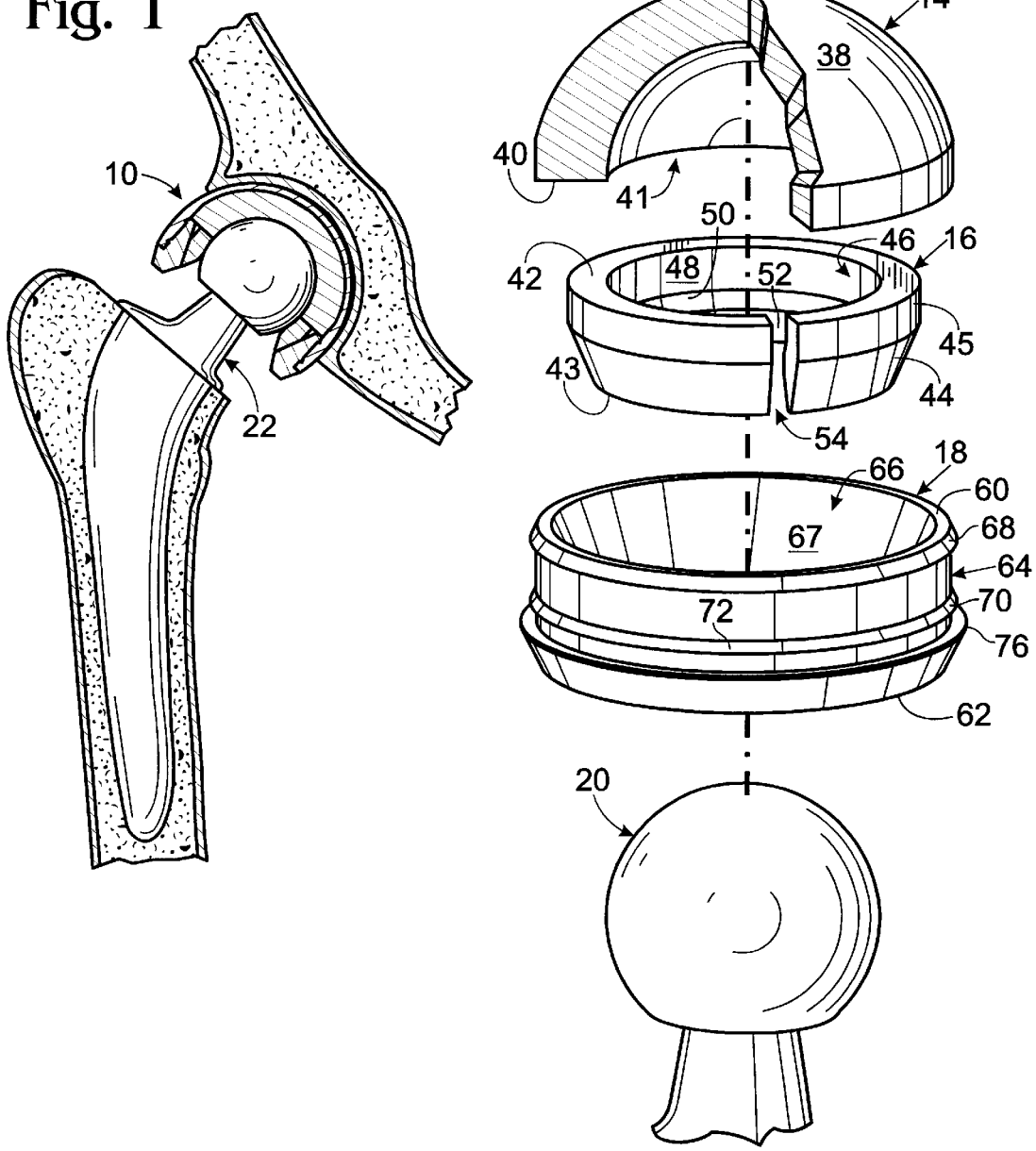

BIPOLAR ACETABULAR CUP

FIELD OF THE INVENTION

The present invention relates to a joint prosthesis and more particularly to an improved bipolar acetabular cup assembly for use in hip-joint replacements.

BACKGROUND OF THE INVENTION

Replacement of the hip joint due to deterioration from aging, illness or traumatic injury has become a relatively common procedure. Unfortunately, due to the complex articulation of the hip joint and the stresses present therein, it is relatively difficult to produce an adequate prosthetic device. More particularly, the natural hip joint can pivot in two directions as well as swivel to a limited extent. This flexibility is due to the ball and socket structure of the joint and has been mimicked by most prosthetics. Moreover, the stress applied in the hip joint and the limited choice of materials which can be used in human implants make it difficult to create a hip prosthesis with adequate durability and resistance to dislocation.

Perhaps because of the many challenges in designing a well-functioning hip replacement, numerous prosthetic devices have been developed for use in hip-joint replacement procedures. A common type of hip prosthetic utilizes a two-part structure including a femoral implant and an acetabular cup. The femoral implant has a head and neck which replace the head and neck of the femur and the acetabular cup fits into the acetabulum in the pelvis and receives the head of the femoral implant. The head on the femoral implant is typically spherically-shaped and is received in a correspondingly-shaped cavity in the cup. This ball and socket configuration replicates the natural flexibility in the hip joint.

As described generally above, significant difficulties arise in the design of a hip joint prosthetic and in some cases an improvement in one area results in a disadvantage in another area. For instance, the head of the femoral implant is typically captured in the acetabular cup by an inwardly projecting lower lip in the cup. Increasing the diameter of this lower lip generally increases the range of motion of the prosthesis, but also makes the joint less resistant to dislocation. Decreasing the size of the opening, on the other hand, can make the device more resistant to dislocation, but also may increase the difficulty of assembly during the operation.

Ease of assembly during operation is an important consideration in the design of a hip joint prosthetic. During the operation, the surgeon first separately installs the femoral implant and the acetabular cup. The head of the implant is then inserted into the cup. Because assembly occurs in the patient, the pieces are relatively hard to grasp. Furthermore, since the cup is normally spherical and polished, it can be particularly difficult to manipulate. Thus, any impediments to assembly are magnified during the installation and great care must be taken to insure that the implant can be easily assembled.

Because hip joint prosthetics occasionally require replacement, it is also important that the surgeon be able to disassemble the device. Moreover, because the surgeon may not know what type of prosthetic has been installed, it is important that the surgeon be able to disassemble the prosthetic without the need for implant-specific tools.

Most acetabular cups utilize a hollow stainless steel or titanium shell into which an ultra-high molecular weight polyethylene liner fits. Some type of deformable structure is formed at the opening of the cup to allow the head of the femoral implant to be inserted and captured. There are two common types of deformable structures that are used. In the first, such as illustrated in U.S. Pat. No. 4,770,658 to Gerimakis, plural fingers are formed in the lower end of the insert. A tapered locking ring fits around the fingers and may be moved between an assembly position where the fingers are free to flex outward to receive the head and a retention position where the fingers are constrained by the locking ring.

In a second type of deformable structure, such as shown in U.S. Pat. No. 4,241,463 to Khovaylo, the liner is formed with an upwardly and outwardly tapering recess to receive a retaining ring. The head, as it is installed, presses the retaining ring upwardly in the recess where it is able to let the head pass through. After the head passes through, the ring contracts down around the bottom of the head. Downward forces on the head simply pull the ring tighter because of the taper. The ring must be lifted back up into the top of the recess to allow the head to be removed. This often requires a special tool because of the confined space.

U.S. Pat. No. 5,062,853 to Forte illustrates, in one embodiment, an implant that combines the locking ring of Gerimakis with the retaining ring of Khovaylo. In Forte, when the locking ring is in a lower position, a recess is left for the retaining ring to expand into. When the locking ring is shifted into an upper position, the recess is eliminated, thereby preventing the locking ring from expanding to receive the femoral implant head. The locking ring includes an exterior rib that fits into a channel in the shell to retain the locking ring in place. Both the locking ring and retaining ring are split in Forte to allow the locking ring to contract sufficiently to disengage the rib from the channel to allow the ring to be moved between the upper and lower positions.

As mentioned above, because of the external rib in Forte, the locking ring must be contracted to be shifted between the upper and lower positions. While the splits in the locking and retaining rings allow this contraction to occur, the retaining ring must not fit too closely against the head or it would not be possible to contract the locking ring or the retaining ring. Therefore, in order to allow the retaining ring to contract, significant play must be left between the retaining ring and the head, which increases wear. Maintaining good conformity to the head is important to reducing wear. Furthermore, any play makes it more likely that the femoral implant head can be accidentally dislocated. Unfortunately, if the play were eliminated in Forte, it would be nearly impossible to retract the locking ring once the head was in the cup.

In addition to requiring some play for operation, the split locking ring in Forte also increases the chance that the ring will jam while being pressed in or removed. The split can also catch and tear the surgeon's glove, with the accompanying increased risk of infection.

It is therefore an object of the present invention to provide an acetabular cup that provides high conformity between the head of the femoral implant and the cup.

It is another object to provide such a cup that has a high lever-out force for the femoral implant head.

One more object of the present invention is to provide an acetabular cup that has a play-free fit with the femoral implant head.

It is also an object of the present invention to provide an acetabular cup in which the flexibility of the joint can be selected as desired.

Another object is to provide an acetabular cup that can be assembled and disassembled easily without special tools.

SUMMARY OF THE INVENTION

The present invention is an acetabular cup assembly for use with a femoral implant having a generally spherical head. The cup includes an outer shell with a generally spherical outer surface, an open end and a cavity extending into the shell from the open end. The cavity has a generally cylindrical section adjacent the open end and a top disposed opposite said open end with the cylindrical section including a first circumferential groove. The cup assembly also includes a bearing liner with an upper surface and a lower surface, with the lower surface including a generally hemispherical pocket configured to receive the spherical head. The bearing liner is configured to be disposed in the cavity in the shell with the upper surface disposed adjacent the top of the cavity and the lower surface facing the open end of the shell. A generally annular retaining ring is provided to be disposed adjacent the lower surface of the bearing liner. The retaining ring includes an inner surface that tapers inwardly and downwardly from the lower surface of the bearing liner toward a pocket opening to form a generally spherical continuation of the hemispherical inner pocket of the bearing liner. The pocket opening has an adjustable perimeter size and the retaining ring also includes an outer surface that tapers inwardly and downwardly from the lower surface of the bearing liner. The cup assembly further includes a generally annular locking ring with an upper end, a lower end, a cylindrical outer surface disposed between the upper end and the lower end and an inner surface that tapers inwardly and downwardly from the upper surface. The cylindrical outer surface includes at least one small circumferential rib and is configured to fit slidably into the cylindrical section of the cavity. The locking ring has a locked configuration in the cavity in which the rib is engaged in the first circumferential groove and the inner surface is disposed closely around the retaining ring to prevent expansion of the perimeter of the pocket opening and thereby prevent passage of the femoral implant head through the pocket opening. The locking ring further has a free configuration in which the locking ring is spaced apart from the bearing liner and the perimeter of the pocket opening is thereby free to expand to pass the femoral implant head. The locking ring is slidable between the locked and free configurations and at least part of the locking ring between the upper and lower ends is formed as a closed loop to prevent radial contraction of the locking ring inner surface as the locking ring is slid between the free and locked configurations.

Many other features, advantages and additional objects of the present invention will become apparent to those versed in the art upon making reference to the detailed description which follows and the accompanying sheets of drawings in which the preferred embodiments incorporating the principles of this invention are disclosed as illustrative examples only.

BRIEF DESCRIPTION OF THE DRAWINGS

FIG. 1 is a cross-sectional view of an acetabular cup constructed according to the present invention.

FIG. 2 is an exploded view of the acetabular cup of FIG. 1 with an outer shell and bearing liner partially broken away.

DETAILED DESCRIPTION OF THE PREFERRED EMBODIMENT

Figure 3A:
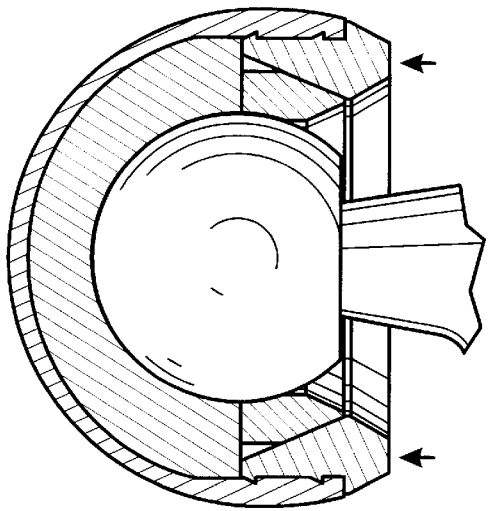
FIGS. 3A–3C are cross-sectional views of the acetabular cup of the present invention showing insertion of a femoral implant head.
Figure 3B:
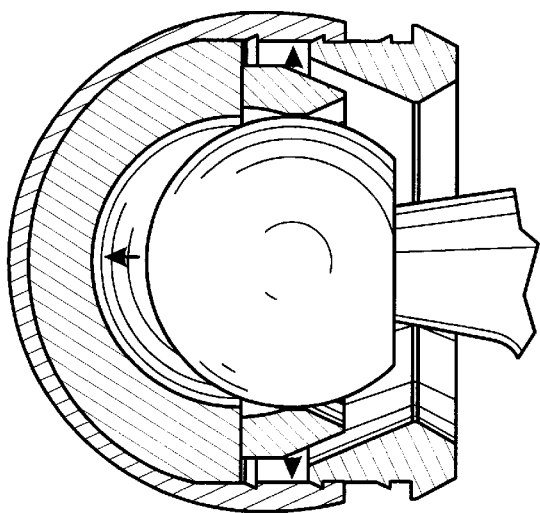

An acetabular cup constructed according to the present invention is shown generally at 10 in FIG. 1. Cup 10 includes an outer shell 12, a bearing liner 14, a retaining ring 16 and a locking ring 18. Cup 10 is configured to fit into the acetabulum of a patient's pelvis and receive and selectively retain a spherical head 20 of a femoral implant 22. Femoral implant 22 is constructed generally according to the prior art.

As shown in FIG. 2, outer shell 12 includes a generally spherical outer surface 24, an open lower end 26 and a cavity 28 extending inwardly from the open lower end. The cavity has a cylindrical section 30 adjacent the lower end and extending up to a hemispherical top 32. An upper circumferential groove 34 and a lower circumferential groove 36 are formed in cylindrical section 30. Outer shell 12 is preferably formed of stainless steel or titanium, with the outer surface being highly polished to allow smooth rotation in the acetabulum.

Bearing liner 14 includes a hemispherical upper surface 38 configured to fit tightly into cavity 28 adjacent the hemispherical top. In the preferred embodiment, the liner is pressed into the shell and held in place by a small rib (not shown), although there are numerous other possibilities for holding the liner in place as will be understood by those of skill in the art.

A lower surface 40 is disposed opposite upper surface 38 and includes a central lower pocket 41 adapted to receive and form a bearing surface for the upper half of femoral implant head 20. Because head 20 and pocket 41 are both spherical in shape, the head is able to rotate and pivot freely within the pocket. Note that the spherical center of the pocket, or its center of curvature, is offset vertically upward from the center of curvature of the outer surface of the shell. As is understood in the art, this tends to urge the shell back to an orientation with the open lower end centered opposite the applied load.

Annular retaining ring 16 floats freely in cavity 28 between bearing liner 14 and locking ring 18. The retaining ring includes an upper surface 42 configured to fit against the lower surface of the bearing liner, a lower surface 43, and an outer surface 44 that tapers inwardly and downwardly from the upper surface. The outer surface includes a cylindrical section 45 adjacent upper surface 42. The cylindrical section allows the retaining ring to expand outward farther than would be the case if the taper were continuous over the entire ring. As will be described below, this expansion is necessary for the femoral implant head to pass into the cup.

An inner surface 46 includes an upper portion 48 that extends inwardly and downwardly from upper surface 42 toward a pocket opening 50. A lower portion 52 extends downwardly and outwardly from the pocket opening to the lower surface.

Upper portion 48 is shaped to form a spherical continuation of pocket 41 to thereby fit around and capture head 20. It should be noted that the extent to which upper portion 48 curves under head 20 controls both the range of pivotal motion of the femoral implant in the cup as well as the security with which the head is captured. For instance, if upper portion 48 curves under head 20 substantially, the head will be more securely captured, but the femoral implant will have less range of motion as well because it will impact lower portion 52 sooner. Thus, the size and angle of the lower portion controls the security and range of motion of the femoral implant. By providing multiple retaining rings with lower portions of different extents, it is possible to provide the surgeon with the option of selecting a desired balance of range of motion and resistance to dislocation.

Retaining ring 16 further includes a radial slot 54 which extends from the outer surface entirely through the retaining ring to the inner surface. The slot permits the ring to flex outward to thereby expand the perimeter of the pocket opening to allow the head to pass therethrough, as shown in FIGS. 3A–3C and 4A–4B.

Locking ring 18 is selectively positionable in cavity 28 to either prevent or allow the retaining ring to expand to pass the head. More particularly, locking ring 18 includes an upper end 60, a lower end 62, a cylindrical outer surface 64 disposed between the upper and lower ends and an inner surface 66 that tapers inwardly and downwardly from the upper surface. Outer surface 64 is sized to closely and slidably fit within cylindrical section 30 of shell 12. When the locking ring is fully engaged in the cavity with upper end 60 disposed against lower surface 40 of bearing liner 14, as shown in FIG. 3C, inner surface 66 fits closely against outer surface 44 of retaining ring 16. This locked position of the locking ring prevents the pocket opening from expanding to pass the head into or out of the cup.

Figure 3C:
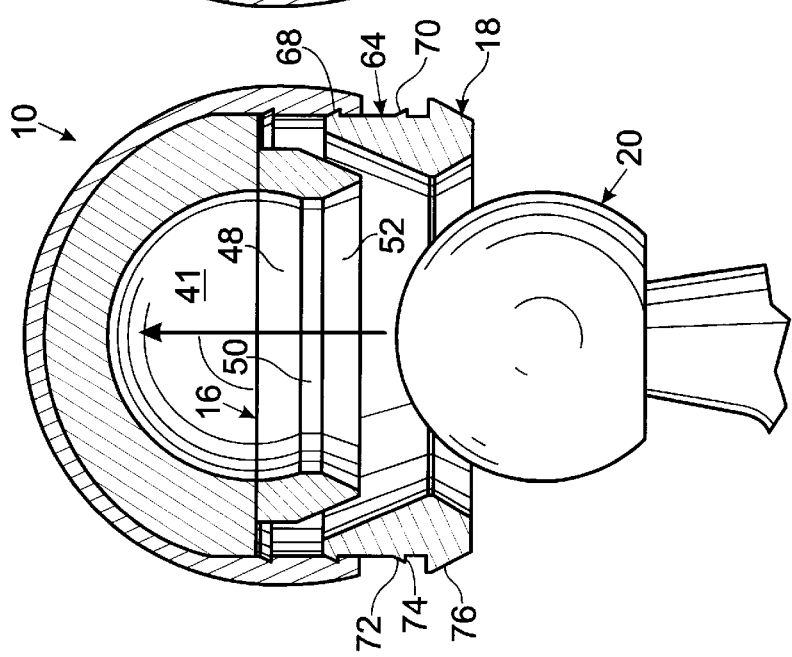
Figure 4A:
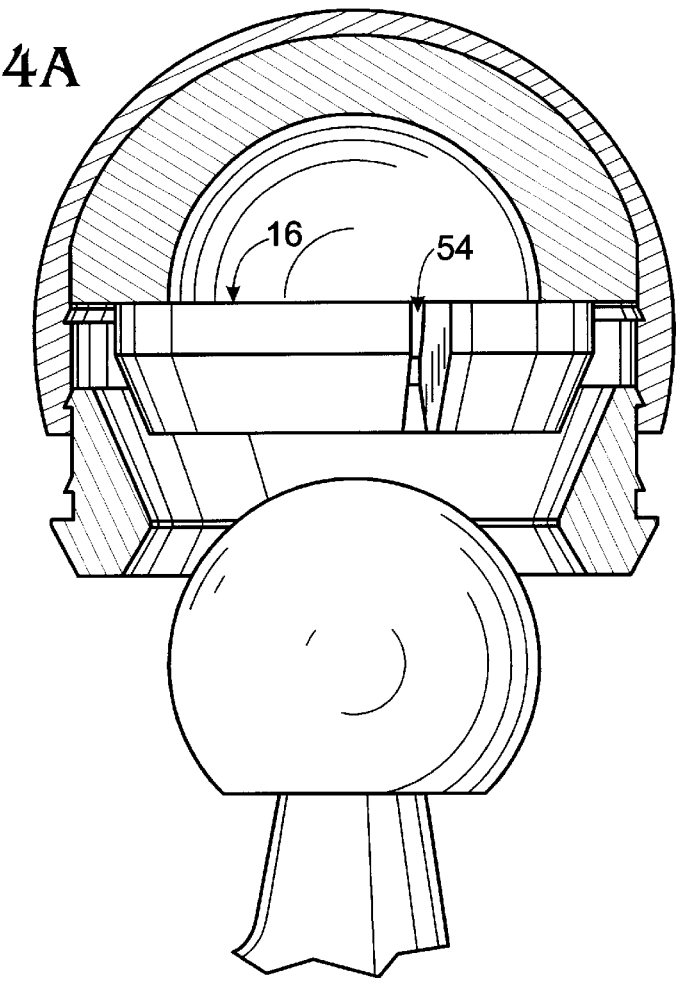
FIGS. 4A–4B are expansion views of a slot in a retaining ring as the formal implant head is inserted into the acetabular cup.
Figure 4B:
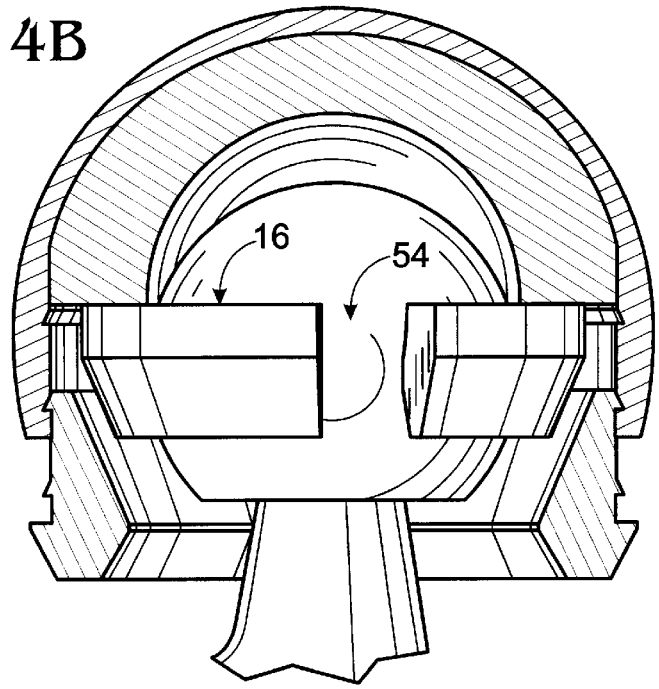

When the locking ring is withdrawn partially from the cavity in a free configuration, as shown in FIG. 3A, the retaining ring, and therefore the pocket opening, is able to expand outwardly to allow the head to pass. Once the head is in place in the cup, the locking ring is shifted up into the locked configuration to secure the head. See FIG. 3C. Note that the locking ring includes a taper 67 which forms a continuation of lower portion 52 to allow maximum range of motion of the femoral implant.

Locking ring 18 is stabilized in cavity 28 by an upper circumferential rib 68 and a lower circumferential rib 70 formed on outer surface 64. When the locking ring is in the free configuration, upper rib 68 engages lower groove 36 to stabilize the locking ring in the free configuration. When the locking ring is located in the locked configuration, upper and lower ribs 68, 70 are engaged in upper and lower grooves 34, 36, respectively. The ribs thus resist movement of the locking ring out of the locked configuration. Note that when the head is installed and locked in the cup and then pulled downwardly, the downward pressure on the retaining ring is converted into outward pressure on the locking ring and inward pressure on the retaining ring by the taper of the interface therebetween. This tightens the locking ring in the cavity and the retaining ring around the femoral implant head and thereby prevents the locking ring from pulling out of the cavity and the head from pulling out past the retaining ring.

Ribs 68 and 70 must be relatively small to allow the locking ring to slide into the cavity without the need for a constriction in diameter of the locking ring. In the preferred embodiment, the ribs have a radial height of about 0.025- inches. Because the locking ring must undergo a localized deformation to allow the ribs to enter the cavity, the ribs are preferably formed with a sloping upper surface 72 to ease entry. A flat lower surface 74 is utilized to increase the force required to pull the ribs out of the grooves to withdraw the locking ring after pushing it into the locked configuration.

Although the ribs are sized to allow the surgeon to push the locking ring into the locked position with finger pressure, a circumferential ledge 76 is provided adjacent the lower end to facilitate removal. Importantly, no special tools are required to remove the locking ring. In particular, a surgeon can use a bone chisel between the ledge and the shell to lever the ring out of the locked position. The ledge is necessary because more force is required to remove the ring than to insert it and there is no area for the surgeon to grip the ring once it is fully installed.

During insertion of the locking ring into the cavity, considerable forces are created on the ribs. As described above, the locking ring is formed as a closed loop to eliminate contraction of the inner surface during installation and removal. However, because the locking ring cannot contract, the ribs must deform during installation. Although the sloping upper surface permits the ribs to enter the cavity without substantial permanent deformation, once installed, the flat lower surface causes the ribs to be significantly disfigured upon removal. This is not a problem because the only time the locking ring is removed is with revision of the hip joint, in which case the entire cup is removed and replaced.

The invented structure provides numerous advantages. In particular, the described structure allows for nearly perfect conformity to the spherical head of the implant over the entire surface area, with no substantial gaps. This is important because accurate conformity is critical to reducing wear on the surface of the plastic bearing.

Use of small ribs on the locking ring also helps to maximize conformity. Because the ribs are small and the locking ring is not split, the ring does not contract in diameter when moved between the locked and free configurations or positions. This means that the retaining ring, which directly abuts the locking ring, also does not need to contract to allow the locking ring to be engaged or disengaged. Thus, because it does not need room to contract, the retaining ring can be fit tightly against the lower portion of the implant head, thereby eliminating the need for any gap or play between the head and the retaining ring to allow for contraction. The use of a solid locking ring also reduces the chance of jamming the ring during installation due to uneven insertion.

The good conformity and play-free fit of the present invention also results in an acetabular cup with a high lever out force. In addition, as described above, a selection of various retaining rings with different diameter openings can be used to provide more or less freedom of movement of the head within the cup.

It will now be clear that an improvement in this art has been provided which accomplishes the objectives set forth above. While the invention has been disclosed in its preferred form, it is to be understood that the specific embodiments which have been depicted and described are not to be considered in a limited sense because there may be other forms which should also be construed to come within the scope of the appended claims.

I claim:

1. An acetabular cup assembly for use with a femoral implant having a generally spherical head, the cup comprising:

an outer shell with a generally spherical outer surface, an open end and a cavity extending into the shell from the open end, the cavity having a generally cylindrical section adjacent the open end and a top disposed opposite said open end, the cylindrical section including a first circumferential groove;

a bearing liner having an upper surface and a lower surface, the lower surface including a generally hemispherical pocket configured to receive the spherical head, the bearing liner configured to be disposed in the cavity in the shell with the upper surface disposed adjacent the top of the cavity and the lower surface facing the open end of the shell;

a generally annular retaining ring configured to be disposed adjacent the lower surface of the bearing liner, the retaining ring including an inner surface that tapers inwardly and downwardly from the lower surface of the bearing liner toward a pocket opening to form a generally spherical continuation of the hemispherical inner pocket of the bearing liner, where the pocket opening has an adjustable perimeter size, the retaining ring further including an outer surface that tapers inwardly and downwardly from the lower surface of the bearing liner; and a generally annular locking ring including an upper end, a lower end, a cylindrical outer surface disposed between the upper end and the lower end and an inner surface that tapers inwardly and downwardly from the upper surface, where the cylindrical outer surface includes at least one small circumferential rib and is configured to fit slidably into the cylindrical section of the cavity, the locking ring having a locked configuration in the cavity in which the rib is engaged in the first circumferential groove and the inner surface is disposed closely around the retaining ring to preventing expansion of the perimeter of the pocket opening and thereby preventing passage of the femoral implant head through the pocket opening, the locking ring further having a free configuration in which the locking ring is spaced apart from the bearing liner and the perimeter of the pocket opening is thereby free to expand to pass the femoral implant head, where the locking ring is slidable during installation and removal between the locked and free configurations and at least part of the locking ring between the upper and lower ends is formed as a closed loop to prevent radial contraction of the locking ring inner surface as the locking ring is slid between the free and locked configurations.

2. The cup assembly of claim 1, wherein the shell includes a second circumferential groove and the rib is engaged in the second circumferential groove when the locking ring is in the free configuration.

3. The cup assembly of claim 2, wherein the locking ring includes at least two circumferential ribs, and one of the ribs is engaged in each of the first and second circumferential grooves when the locking ring is in the locked configuration.

4. The cup assembly of claim 2, wherein the retaining ring is slotted to permit the perimeter of the pocket opening to expand to pass the femoral implant head when the locking ring is in the free configuration.

5. The cup assembly of claim 2, wherein the locking ring further includes an outwardly projecting circumferential ledge disposed adjacent the lower end, the ledge being configured to fit against the lower end of the shell when the locking ring is in the locked configuration.

6. The cup assembly of claim 2, wherein the circumferential rib on the locking ring projects radially approximately 0.025-inches above the cylindrical outer surface and includes a flat lower surface that projects radially away from the cylindrical outer surface, the rib further including a sloping upper surface.

7. The cup assembly of claim 1, wherein the retaining ring is slotted to permit the perimeter of the pocket opening to expand to pass the femoral implant head when the locking ring is in the free configuration.

8. The cup assembly of claim 7, wherein the retaining ring includes one vertically oriented slot radially severing the retaining ring at one location on the perimeter thereof.

9. The cup assembly of claim 7, wherein the locking ring further includes an outwardly projecting circumferential ledge disposed adjacent the lower end, the ledge being configured to fit against the lower end of the shell when the locking ring is in the locked configuration.

10. The cup assembly of claim 7, wherein the circumferential rib on the locking ring projects radially approximately 0.025-inches above the cylindrical outer surface and includes a flat lower surface that projects radially away from the cylindrical outer surface, the rib further including a sloping upper surface.

11. The cup assembly of claim 1, wherein the locking ring further includes an outwardly projecting circumferential ledge disposed adjacent the lower end, the ledge being configured to fit against the lower end of the shell when the locking ring is in the locked configuration.

12. The cup assembly of claim 1, wherein the circumferential rib on the locking ring projects radially approximately 0.025-inches above the cylindrical outer surface.

13. The cup assembly of claim 12, wherein the at least one rib includes a flat lower surface that projects radially away from the cylindrical outer surface.

14. The cup assembly of claim 12, wherein the at least one rib includes a sloping upper surface.

15. The cup assembly of claim 1, wherein the entire locking ring is formed as a unitary closed loop.

16. A joint prosthesis comprising:

a femoral implant having a generally spherical head and being adapted to replace the femoral head of a femur; and an acetabular cup assembly including:

an outer shell with a generally spherical outer surface, an open end and a cavity extending into the shell from the open end, the cavity having a generally cylindrical section adjacent the open end and a top disposed opposite said open end, the cylindrical section including a first circumferential groove;

a bearing liner having an upper surface and a lower surface, the lower surface including a generally hemispherical pocket configured to receive the spherical head, the bearing liner configured to be disposed in the cavity in the shell with the upper surface disposed adjacent the top of the cavity and the lower surface facing the open end of the shell;

a generally annular retaining ring configured to be disposed adjacent the lower surface of the bearing liner, the retaining ring including an inner surface that tapers inwardly and downwardly from the lower surface of the bearing liner toward a pocket opening to form a generally spherical continuation of the hemispherical inner pocket of the bearing liner, where the pocket opening has an adjustable perimeter size, the retaining ring further including an outer surface that tapers inwardly and downwardly from the lower surface of the bearing liner; and a generally annular locking ring including an upper end, a lower end, a cylindrical outer surface disposed between the upper end and the lower end and an inner surface that tapers inwardly and downwardly from the upper surface, where the cylindrical outer surface includes at least one small circumferential rib and is configured to fit slidably into the cylindrical section of the cavity, the locking ring having a locked configuration in the cavity in which the rib is engaged in the first circumferential groove and the inner surface is disposed closely around the retaining ring to prevent expansion of the perimeter of the pocket opening and thereby preventing passage of the femoral implant head through the pocket opening, the locking ring further having a free configuration in which the locking ring is spaced apart from the bearing liner and the perimeter of the pocket opening is thereby free to expand to pass the femoral implant head, where the locking ring is slidable during installation and removal between the locked and free configurations and at least part of the locking ring between the upper and lower ends is formed as a closed loop to prevent radial contraction of the locking ring inner surface as the locking ring is slid between the free and locked configurations.

17. An acetabular cup assembly for use with a femoral implant having a generally spherical head, the cup comprising:

an outer shell with a generally spherical outer surface, an open end and a cavity extending into the shell from the open end, the cavity having a generally cylindrical section adjacent the open end and a top disposed opposite said open end, the cylindrical section including a first circumferential groove and a second circumferential groove spaced apart from the first groove;

a bearing liner having an upper surface and a lower surface, the lower surface including a generally hemispherical pocket configured to receive the spherical head, the bearing liner configured to be disposed in the cavity in the shell with the upper surface disposed adjacent the top of the cavity and the lower surface facing the open end of the shell;

a generally annular retaining ring configured to be disposed adjacent the lower surface of the bearing liner, the retaining ring including an inner surface that tapers inwardly and downwardly from the lower surface of the bearing liner toward a pocket opening to form a generally spherical continuation of the hemispherical inner pocket of the bearing liner, where the pocket opening has an adjustable perimeter size, the retaining ring further including an outer surface that tapers inwardly and downwardly from the lower surface of the bearing liner; and a generally annular locking ring including an upper end, a lower end, a cylindrical outer surface disposed between the upper end and the lower end and an inner surface that tapers inwardly and downwardly from the upper surface, where the cylindrical outer surface includes first and second small circumferential ribs and is configured to fit slidably into the cylindrical section of the cavity, the locking ring having a locked configuration in the cavity in which the first and second ribs are engaged in the first and second circumferential grooves and the inner surface is disposed closely around the retaining ring to prevent expansion of the perimeter of the pocket opening and thereby prevent passage of the femoral implant head through the pocket opening, the locking ring further having a free configuration in which the locking ring is spaced apart from the bearing liner with the first rib engaged in the second groove and the perimeter of the pocket opening is thereby free to expand to pass the femoral implant head, where the locking ring is slidable during installation and removal between the locked and free configurations and at least part of the locking ring between the upper and lower ends is formed as a closed loop to prevent radial contraction of the locking ring inner surface as the locking ring is slid between the free and locked configurations.

\* \* \* \* \*